(12) United States Patent
Mazoyer et al.

(10) Patent No.: US 11,091,419 B2
(45) Date of Patent: Aug. 17, 2021

(54) PREPARATION AND PURIFICATION OF BIPHENYLDICARBOXYLIC ACIDS

(71) Applicant: ExxonMobil Chemical Patents Inc., Baytown, TX (US)

(72) Inventors: Etienne Mazoyer, Woluwe Saint Pierre (BE); Monica D. Lotz, Houston, TX (US); Constantinos P. Bokis, The Woodlands, TX (US); Javier Guzman, Porter, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/652,894

(22) PCT Filed: May 11, 2018

(86) PCT No.: PCT/US2018/032210
§ 371 (c)(1),
(2) Date: Apr. 1, 2020

(87) PCT Pub. No.: WO2019/103756
PCT Pub. Date: May 31, 2019

(65) Prior Publication Data
US 2020/0361847 A1 Nov. 19, 2020

Related U.S. Application Data

(60) Provisional application No. 62/589,658, filed on Nov. 22, 2017.

(51) Int. Cl.
*C07C 51/43* (2006.01)

(52) U.S. Cl.
CPC .................................. *C07C 51/43* (2013.01)

(58) Field of Classification Search
CPC ......... C07C 51/43; C07C 51/41; C07C 53/06; C25B 3/25; C25B 11/043; C25B 11/057;
(Continued)

(56) References Cited

U.S. PATENT DOCUMENTS 3,584,039 A 6/1971 Meyer
4,476,242 A 10/1984 Puskas et al.
(Continued)

FOREIGN PATENT DOCUMENTS

EP 0 668 262 8/1995
JP 2002-128729 5/2002
(Continued)

*Primary Examiner* — Deborah D Carr

(57) ABSTRACT

Processes are described for purifying a biphenyldicarboxylic acid product containing one or more impurities, particularly at least formylbiphenylcarboxylic acid. In the processes, a mixture comprising the biphenyldicarboxylic acid product is contacted with hydrogen in the presence of a hydrogenation catalyst under conditions to selectively reduce at least part of the formylbiphenylcarboxylic acid to produce a hydrogenation effluent comprising (i) hydroxymethylbiphenylcarboxylic acid and/or methylbiphenylcarboxylic acid, and (ii) biphenylcarboxylic acid. At least a portion of the biphenyldicarboxylic acid is then separated from the hydrogenation effluent. Advantageously, a polyester product may be produced from the separated biphenyldicarboxylic acid.

22 Claims, 2 Drawing Sheets

(58) Field of Classification Search
CPC .................. B01J 31/181; B01J 2531/26; B01J 2531/0238; B01J 31/1815
USPC ........................................................ 562/459
See application file for complete search history.

(56) References Cited

U.S. PATENT DOCUMENTS

| | | | |
|---|---|---|---|
| 6,541,662 | B2 | 4/2003 | Machida et al. |
| 6,642,407 | B2 | 11/2003 | Rao et al. |
| 7,005,540 | B2 | 2/2006 | Komatsu et al. |
| 7,485,746 | B2 | 2/2009 | Belmonte et al. |
| 7,547,803 | B2 | 6/2009 | Nagao et al. |
| 7,935,844 | B2 | 5/2011 | Bartos |
| 7,935,845 | B2 | 5/2011 | Bartos et al. |
| 8,173,834 | B2 | 5/2012 | Bartos |
| 8,492,583 | B2 | 7/2013 | Nubel et al. |
| 8,624,055 | B2 | 1/2014 | Schammel et al. |
| 9,085,669 | B2 | 7/2015 | Dakka et al. |
| 9,580,572 | B2 | 2/2017 | Dakka et al. |
| 9,663,417 | B2 | 5/2017 | Dakka et al. |
| 2002/0002303 | A1 | 1/2002 | Rosen |
| 2004/0260052 | A1* | 12/2004 | Nagao .................. C07C 51/43 528/271 |
| 2009/0069594 | A1 | 3/2009 | Gong et al. |
| 2012/0178964 | A1 | 7/2012 | Nubel et al. |
| 2015/0080545 | A1 | 3/2015 | Dakka et al. |
| 2015/0182890 | A1 | 7/2015 | Keyes et al. |
| 2015/0183709 | A1 | 7/2015 | Bartos |
| 2015/0183710 | A1 | 7/2015 | Clark et al. |
| 2015/0183713 | A1 | 7/2015 | Bartos |

FOREIGN PATENT DOCUMENTS

| | | |
|---|---|---|
| JP | 06-211740 | 8/2006 |
| JP | 06-211744 | 8/2006 |
| JP | 09-025257 | 2/2009 |
| TW | 201736432 | 10/2017 |
| WO | WO 2006/085134 | 8/2006 |
| WO | WO 2015/112252 | 7/2015 |
| WO | WO 2017/112031 | 6/2017 |

* cited by examiner

PREPARATION AND PURIFICATION OF BIPHENYLDICARBOXYLIC ACIDS

CROSS-REFERENCE OF RELATED APPLICATIONS

This application is a Section 371 National Phase entry of International Application No. PCT/US2018/032210 filed May 11, 2018, which claims the benefit of U.S. Provisional Application No. 62/589,658, filed Nov. 22, 2017, the disclosures of which are incorporated herein by reference.

FIELD

This disclosure relates to preparation and purification of biphenyldicarboxylic acids (BPDAs), and polyester products produced therefrom.

BACKGROUND

BPDAs, especially the 3,4' and 4,4' isomers, are useful intermediates in the production of a variety of commercially valuable products, including polyesters and plasticizers for PVC and other polymer compositions. For example, BPDAs can be converted to ester plasticizers by esterification with a long chain alcohol. In addition, biphenyldicarboxylic acids are potential precursors, either alone or as a modifier for polyethylene terephthalate (PET), in the production of polyester fibers, engineering plastics, liquid crystal polymers for electronic and mechanical devices, and films with high heat resistance and strength. The 4,4' isomer is the most desired for this service due to the advantageous properties of the resulting polymers.

As disclosed in U.S. Pat. Nos. 9,580,572 and 9,663,417, the entire disclosures of which are incorporated herein by reference in their entirety, BPDAs may be produced by hydroalkylation of toluene followed by dehydrogenation of the resulting (methylcyclohexyl)toluene (MCHT) to produce dimethylbiphenyl (DMBP) compounds. The DMBP compounds can then be oxidized to the desired diacids by reaction with an oxidant, such as oxygen, ozone or air, or any other oxygen source, such as hydrogen peroxide, in the presence of a catalyst, such as Co and/or Mn, at temperatures from 30° C. to 300° C.

Alternative routes via benzene are described in U.S. Pat. No. 9,085,669, the entire disclosure of which is incorporated herein by reference, in which the benzene is initially converted to biphenyl, either by oxidative coupling or by hydroalkylation to cyclohexylbenzene (CHB) followed by dehydrogenation of the CHB, and then the biphenyl is alkylated with methanol. The resultant DMBP compounds can then be oxidized to the desired diacids by the method described above.

One problem with existing routes to biphenyldicarboxylic acids through DMBP compounds is that the oxidation step, in addition to producing the desired diacids, also inevitably produces certain by-products, such as formylbiphenylcarboxylic acid (FBCA), fluorenones and quinones that, if not removed, can (a) reduce polymer growth by chain termination when the BPDA is subsequently polymerized, and (b) be detrimental to the color of the resultant polymer. Moreover, the nature of the BPDA (i.e. low volatility and formation of solid solutions) means that typical physical separation techniques (e.g. distillation and crystallization) are generally not effective in purifying the crude diacid.

There is, therefore, interest in developing alternative processes for purifying BPDAs produced by oxidation of DMBP compounds.

Additional potential reference of interest include: U.S. Pat. Nos. 7,485,746, 7,935,844, 7,935,845, 8,173,834, 8,492,583, 8,624,055, 3,584,039, and 4,476,242; US 2009/0069594, 2012/0178964, 2015/0183709, 2015/0183713, 2015/0183710, 2015/0183709, 2015/0182890, and 2015/0080545; WO 2015/112252 and WO 2006/085134.

SUMMARY

According to the present disclosure, it has now been found that a purified BPDA product can be produced from a crude product (typically obtained from the oxidation of DMBP) comprising BPDA and at least one impurity (typically formylbiphenylcarboxylic acid), by combining the crude product with a liquid, such as water, to produce a mixture (typically a solution or slurry) and then contacting the mixture with hydrogen in the presence of a hydrogenation catalyst. By these steps, the FBCA and color-forming impurities in the crude product can be selectively reduced in such a way that they can be converted to more preferable compounds (e.g., non-color-forming compounds) and/or separated easily from the BPDA (e.g. by crystallization). As a result a purified BPDA product can be produced.

Thus, in any embodiment the present disclosure provides a process for purifying a biphenyldicarboxylic acid product containing formylbiphenylcarboxylic acid, the process comprising (or consisting of, or consisting essentially of):
  (a1) contacting a mixture comprising the biphenyldicarboxylic acid product with hydrogen in the presence of a hydrogenation catalyst under conditions effective to selectively reduce at least part of the formylbiphenylcarboxylic acid and produce a hydrogenation effluent comprising (i) hydroxymethylbiphenylcarboxylic acid and/or methylbiphenylcarboxylic acid, and (ii) biphenyldicarboxylic acid; and
  (b1) separating at least a portion of the biphenyldicarboxylic acid from the hydrogenation effluent.

Also in any embodiment the present disclosure provides a polyester product comprising the reaction product of a diol with at least one of the following;
  (i) the biphenyldicarboxylic acid separated in (b1); and/or
  (ii) a biphenyldiester product formed from the esterification of the biphenyldicarboxylic acid separated in (b1).

Also in any embodiment, the present disclosure provides a process for producing 3,4'- and/or 4,4'-biphenyldicarboxylic acid, the process comprising (or consisting of, or consisting essentially of):
  (a2) contacting 3,4'- and/or 4,4'-dimethylbiphenyl with a source of oxygen in the presence of an oxidation catalyst to produce an oxidation product comprising (i) 3,4'- and/or 4,4'-biphenyldicarboxylic acid and (ii) one or more isomers of formylbiphenylcarboxylic acid;
  (b2) combining at least a portion of the oxidation product with a liquid to produce a product mixture;
  (c2) contacting the product mixture with hydrogen in the presence of a hydrogenation catalyst under conditions effective to selectively reduce at least part of the formylbiphenylcarboxylic acid and produce a hydrogenation effluent comprising (i) hydroxymethylbiphenylcarboxylic acid and/or methylbiphenylcarboxylic acid and (ii) 3,4'- and/or 4,4'-biphenyldicarboxylic acid; and (d2) separating at least a portion of the 3,4'- and/or 4,4'-biphenyldicarboxylic acid from the hydrogenation effluent.

DETAILED DESCRIPTION OF THE PREFERRED EMBODIMENTS

Figure 1:
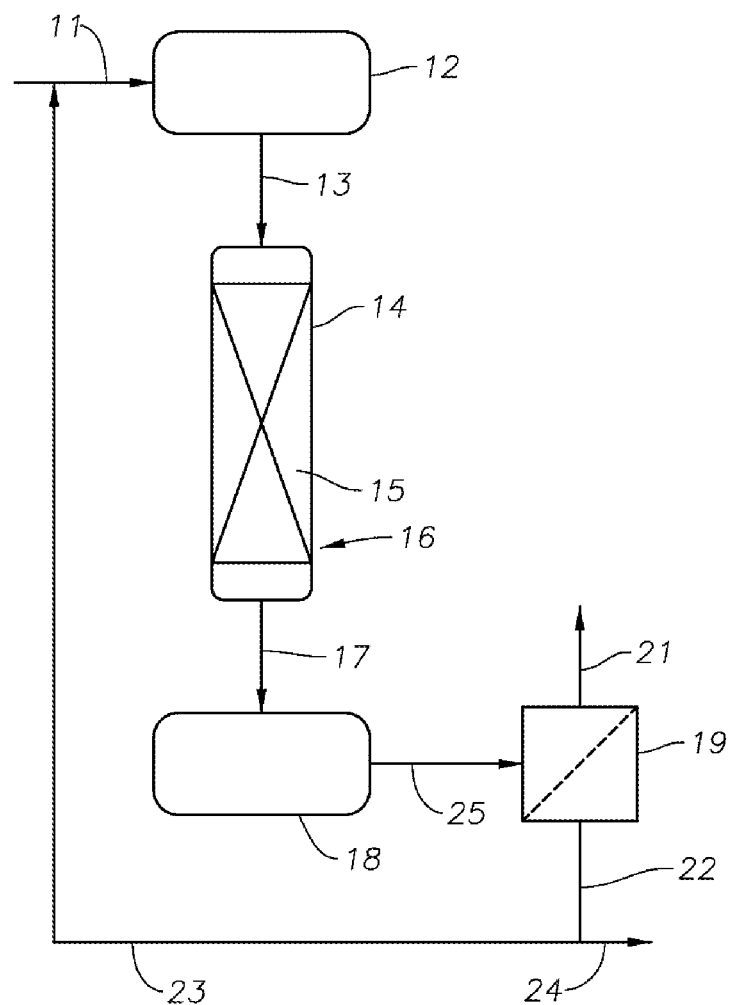
FIG. 1 is a flow diagram of a process for purifying the crude oxidation product of 4,4'-dimethylbiphenyl according to one or more embodiments of the present disclosure.

As used herein, "wt %" means percentage by weight, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, the concentrations of the various components of the first mixture are expressed based on the total weight of the first mixture. All ranges expressed herein should include both end points as two specific embodiments unless specified or indicated to the contrary.

Unless otherwise indicated, room temperature is 23° C.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6$^{th}$ Edition, by F. Albert Cotton et al. (John Wiley & Sons, Inc., 1999).

The present disclosure relates to processes for producing a purified biphenyldicarboxylic acid (BPDA) product from a crude product comprising BDPA and at least one impurity, typically at least formylbiphenylcarboxylic acid (FBCA). Preferably, the crude product is derived from the catalytic oxidation of at least one dimethylbiphenyl (DMBP) compound. The purification processes described herein typically comprise combining the crude oxidation product with a liquid to form a mixture, typically a solution or slurry, and then contacting the resulting mixture with hydrogen in the presence of a hydrogenation catalyst and under conditions effective to selectively reduce at least part of the FBCA and produce a hydrogenation effluent comprising (i) hydroxymethylbiphenylcarboxylic acid (HBCA) and/or methylbiphenylcarboxylic acid (MBCA), and (ii) BDPA. Whereas BPDA readily forms solid solutions with FBCA, it has been found that the difference in geometry between BPDA and HBCA/MBCA effectively avoids the formation of solid solutions between the compounds. As a result, BPDA containing less than 200 ppmw, preferably less than 20 ppmw, of FBCA, HBCA, and/or MBCA, can readily be separated from the hydrogenation effluent, for example by crystallization. The processes described herein are particularly effective in purifying 3,4'- and/or 4,4'-BPDA produced by oxidation of 3,4'- and/or 4,4'-DMBP.

Production of Biphenyldicarboxylic Acid

As discussed above, the present processes are particularly directed towards the purification of a crude product (typically obtained from the oxidation, preferably catalytic oxidation, of DMBP) comprising BPDA and at least one impurity (typically FBCA). Any known method can be used to produce the DMBP starting material but, in one or more embodiments, a preferred process initially involves the conversion of toluene to (methylcyclohexyl)toluene (MCHT) in the presence of hydrogen over a hydroalkylation catalyst according to the following reaction:

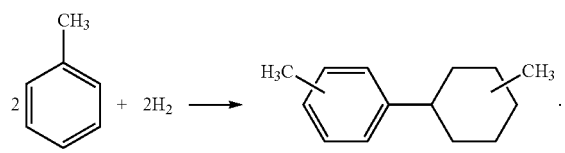

The MCHT can then be dehydrogenated to produce the desired DMBP product.

The catalyst employed in the hydroalkylation reaction is generally a bifunctional catalyst comprising a hydrogenation component and a solid acid alkylation component, typically a molecular sieve. The catalyst may also include a binder such as clay, alumina, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Any known hydrogenation metal or compound thereof can be employed as the hydrogenation component of the catalyst, although suitable metals include palladium, ruthenium, nickel, zinc, tin, and cobalt, with palladium being particularly advantageous. In certain embodiments, the amount of hydrogenation metal present in the catalyst is between 0.05 and 10 wt %, such as between 0.1 and 5 wt %, of the catalyst.

Often, the solid acid alkylation component comprises a large pore molecular sieve having a Constraint Index (as defined in U.S. Pat. No. 4,016,218) of less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-4 is described in U.S. Pat. No. 4,021,447. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

More preferably, the solid acid alkylation component comprises a molecular sieve of the MCM-22 family. The term "MCM-22 family material" (or "material of the MCM- 22 family" or "molecular sieve of the MCM-22 family"), as used herein, includes one or more of: molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the ATLAS OF ZEOLITE FRAMEWORK TYPES (Fifth edition, 2001), the entire content of which is incorporated as reference); molecular sieves made from a common second degree building block, being a 2-dimensional tiling of such MWW framework topology unit cells, forming a monolayer of one unit cell thickness, preferably one c-unit cell thickness; molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0293032), ITQ-1 (described in U.S. Pat. No. 6,077,498), ITQ-2 (described in WO97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof.

In addition to the toluene and hydrogen, the feed to the hydroalkylation reaction may include benzene and/or xylene which can undergo hydroalkylation to produce various methylated cyclohexylbenzene molecules having 12 to 16 carbon atoms. A diluent, which is substantially inert under hydroalkylation conditions, may also be included in the hydroalkylation feed. In certain embodiments, the diluent is a hydrocarbon, in which the desired cycloalkylaromatic product is soluble, such as a straight chain paraffinic hydrocarbon, a branched chain paraffinic hydrocarbon, and/or a cyclic paraffinic hydrocarbon. Examples of suitable diluents are decane and cyclohexane. Although the amount of diluent is not narrowly defined, desirably the diluent is added in an amount such that the weight ratio of the diluent to the aromatic compound is at least 1:100; for example at least 1:10, but no more than 10:1, desirably no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are from 100° C. to 400° C., such as from 125° C. to 250° C., while suitable reaction pressures are between 100 and 7,000 kPa, such as between 500 and 5,000 kPa. The molar ratio of hydrogen to aromatic feed is typically from 0.15:1 to 15:1.

It has been found that MCM-22 family molecular sieves are particularly active and stable catalysts for the hydroalkylation of toluene. In addition, catalysts containing MCM-22 family molecular sieves exhibit improved selectivity to the 3,3'-dimethyl, the 3,4'-dimethyl, the 4,3'-dimethyl and the 4,4'-dimethyl isomers in the hydroalkylation product, while at the same time reducing the formation of fully saturated and heavy by-products. For example, using an MCM-22 family molecular sieve with a toluene feed, it is found that the hydroalkylation reaction product may comprise: at least 60 wt %, such as at least 70 wt %, for example at least 80 wt % of the 3,3', 3,4', 4,3' and 4,4'-isomers of MCHT based on the total weight of all the MCHT isomers; less than 40 wt %, such as less than 30 wt %, for example from 15 to 25 wt % of the 2,2', 2,3', and 2,4'-isomers of MCHT based on the total weight of all the MCHT isomers; less than 30 wt % of methylcyclohexane and less than 2% of dimethylbicyclohexane compounds; and less than 1 wt % of compounds containing in excess of 14 carbon atoms, such as di(methylcyclohexyl)toluene.

The hydroalkylation reaction product may also contain significant amounts of residual toluene, for example up to 50 wt %, such as up to 90 wt %, typically from 60 to 80 wt % of residual toluene based on the total weight of the hydroalkylation reaction product. The residual toluene can readily be removed from the reaction effluent by, for example, distillation. The residual toluene can then be recycled to the hydroalkylation reactor, together with some or all of any unreacted hydrogen. In some embodiments, it may be desirable to remove the $C_{14+}$ reaction products, such as di(methylcyclohexyl)toluene, by distillation.

The remainder of the hydroalkylation reaction effluent, composed mainly of (methylcyclohexyl)toluenes, is then dehydrogenated to convert the (methylcyclohexyl)toluenes to the corresponding methyl-substituted biphenyl compounds. The dehydrogenation is conveniently conducted at a temperature from 200° C. to 600° C. and a pressure from 100 kPa to 3550 kPa (atmospheric to 500 psig) in the presence of dehydrogenation catalyst. A suitable dehydrogenation catalyst comprises one or more elements or compounds thereof selected from Group 10 of the Periodic Table of Elements, for example platinum, on a support, such as silica, alumina or carbon nanotubes. In any embodiment, the Group 10 element is present in an amount from 0.1 to 5 wt % of the catalyst. In some cases, the dehydrogenation catalyst may also include tin or a tin compound to improve the selectivity to the desired methyl-substituted biphenyl product. In any embodiment, the tin is present in an amount from 0.05 to 2.5 wt % of the catalyst.

Particularly using an MCM-22 family-based catalyst for the upstream hydroalkylation reaction, the product of the dehydrogenation step comprises DMBP compounds in which the concentration of the 3,3'-, 3,4'- and 4,4' isomers is at least 50 wt %, such as at least 60 wt %, for example at least 70 wt % based on the total weight of DMBP compounds. Typically, the concentration of the 2,X'-DMBP isomers in the dehydrogenation product is less than 50 wt %, such as less than 30 wt %, for example from 5 to 25 wt % based on the total weight of DMBP compounds.

In other embodiments of the present processes, the DMBP starting material can be produced from benzene via conversion of the benzene to diphenyl followed by methylation of the biphenyl to DMBP. For example, it is known that benzene can be converted directly to biphenyl by reaction with oxygen over an oxidative coupling catalyst as follows:

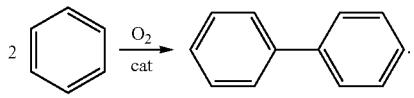

Details of the oxidative coupling of benzene can be found in Ukhopadhyay, Sudip; Rothenberg, Gadi; Gitis, Diana; Sasson, Yoel, Casali INSTITUTE OF APPLIED CHEMISTRY, Hebrew University of Jerusalem, Israel, 65(10) JOURNAL OF ORGANIC CHEMISTRY 3107-3110 (2000), incorporated herein by reference.

Alternatively, benzene can be converted to biphenyl by hydroalkylation to cyclohexylbenzene according to the reaction:

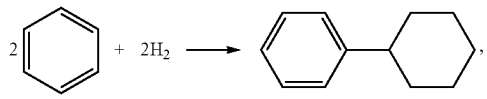

followed by dehydrogenation of the cyclohexylbenzene.

In such a process, the benzene hydroalkylation can be conducted in the same manner as described above for the hydroalkylation of toluene, while the dehydrogenation of the cyclohexylbenzene can be conducted in the same manner as described above for the dehydrogenation of (methylcyclohexyl)toluene.

In either case, the biphenyl product of the oxidative coupling step or the hydroalkylation/dehydrogenation sequence is then methylated, for example with methanol, to produce DMBP. Any known alkylation catalyst can be used for the methylation reaction, such as an intermediate pore molecular sieve having a Constraint Index (as defined in U.S. Pat. No. 4,016,218) of 3 to 12, for example ZSM-5.

The composition of the methylated product will depend on the catalyst and conditions employed in the methylation reaction, but inevitably will comprise a mixture of the different isomers of DMBP. Typically, the methylated product will contain from 50 to 100 wt % of 3,3'-, 3,4'- and 4,4'-DMBP isomers and from 0 to 50 wt % of 2,X' (where X' is 2', 3' or 4')-DMBP isomers based on the total weight of DMBP compounds in the methylation product.

Irrespective of the process used to produce the DMBP starting material, the raw dimethylbiphenyl product from the production sequences described above will contain unreacted components and by-products in addition to a mixture of DMBP isomers. For example, where the initial feed comprises toluene and the production sequence involves hydroalkylation to MCHT and dehydrogenation of the MCHT, the raw DMBP product will tend to contain residual toluene and MCHT as well as by-products including hydrogen, methylcyclohexane dimethylcyclohexylbenzene, and $C_{15+}$ heavy hydrocarbons in addition to the target DMBP isomers. Thus, in some embodiments, prior to any separation of the DMBP isomers, the raw product of the MCHT dehydrogenation is subjected to a rough cut separation to remove at least part of the residues and by-products with significantly different boiling points from the DMBP isomers. For example, the hydrogen by-product can be removed and recycled to the hydroalkylation and/or MCHT dehydrogenation steps, while residual toluene and methylcyclohexane by-product can be removed and recycled to the hydroalkylation step. Similarly, part of the heavy ($C_{15+}$) components can be removed in the rough cut separation and can be recovered for use as a fuel or can be reacted with toluene over a transalkylation catalyst to convert some of the dialkylate to additional MCHT. A suitable rough cut separation can be achieved by distillation. For example, the $H_2$ and $C_7$ components can be stripped from the $C_{12+}$ components without reflux.

After partial removal of the by-products and residual components in the rough cut separation, the remaining dimethylbiphenyl product is typically subjected to a first DMBP separation step, in which the product is separated into at least a first stream rich in 3,4' and 4,4' DMBP and at least one second stream comprising one or more 2,x' (where x' is 2', 3', or 4') and 3,3' DMBP isomers. The second stream will also typically contain most of the unreacted MCHT and most of the dimethylcyclohexylbenzene by-product in the raw dimethylbiphenyl product. A suitable process for effecting this initial separation is crystallization and/or distillation operating below or at atmospheric pressure.

In certain embodiments, part or all of the first stream can be recovered and, optionally after further purification, can be oxidized to produce BPDA as described below. Additionally or alternatively, part or all of the first stream may be subjected to a second DMBP separation step to separate the first stream into a third stream rich in 4,4' DMBP and a fourth stream comprising 3,4' DMBP. Because of the differences in fusion temperatures of these isomers, the second DMBP separation is conveniently effected by fractional crystallization. In some embodiments, the fractional crystallization is assisted by the addition of a solvent, preferably a $C_3$ to $C_{12}$ aliphatic hydrocarbon, more preferably pentane and/or hexane, to the first stream. Either or both of the third and fourth streams can then be oxidized to produce BPDA as described below.

In some embodiments the second stream, 2,x' (where x' is 2', 3', or 4') and 3,3' DMBP isomers, can undergo further treatment, such as isomerization to increase the concentration of the more desirable 3,4', and especially 4,4', isomer.

Any of the DMBP isomer-containing streams described above can be oxidized to produce the corresponding biphenyldicarboxylic acid. Preferably, the DMBP isomer-containing stream is rich in 3,4' and/or 4,4' DMBP, such as the first, third, and fourth streams described above. Particularly preferably, the DMBP isomer-containing stream is rich in 4,4' DMBP, such as the third stream described above. For example, the DMBP isomer-containing stream preferably comprises at least 50 wt % of 3,4' and/or 4,4' DMBP (more preferably 4,4' DMBP), such as at least 75 wt %, or at least 90 wt % of 3,4' and/or 4,4' DMBP (more preferably 4,4' DMBP). The oxidation can be performed by any process known in the art, such as via thermal or catalytic methods. Preferably, the oxidation can be performed by reacting the methyl-substituted biphenyl compounds with an oxidant, such as oxygen, ozone or air, or any other oxygen source, such as hydrogen peroxide, in the presence of a catalyst and with or without a promoter, such as Br, at temperatures from 30° C. to 300° C., such as from 60° C. to 200° C. Suitable catalysts comprise Co or Mn or a combination of both metals, such as cobalt acetate or cobalt (II) chloride hexahydrate. The oxidation is normally conducted with the DMBP isomer(s) being in solution, generally in acetic acid as solvent. Generally, in such aspects BPDA is formed in a solid state within the solution. Typically, a solid crude BPDA containing product is then separated from the solution via a solid liquid separation, e.g., filtration. Often, the crude BPDA containing product further comprises trace amounts of the oxidation catalyst and/or promoter. The resulting liquid phase, i.e., the oxidation mother liquor, typically comprises the solvent (such as acetic acid), unreacted feed compound(s), and the remainder of the catalyst and/or promoter.

Purification of Biphenyldicarboxylic (BPDA) Product

Typically, the crude product from the oxidation of DMBP will contain 50 wt % or more, preferably 75 wt % or more, more preferably 90 wt % or more, and ideally 95 wt % or more of BPDA. The relative amounts of the BPDA isomers in the crude product will vary depending on the composition of the oxidized DMBP stream. For example, in the oxidation of a 4,4' DMBP rich stream, 4,4' BPDA will be the predominant BPDA isomer, e.g., greater than 50 wt % of the total weight BPDA compounds in the crude product. Typically, the crude product will contain from 50 to 100 wt % of 3,4'- and/or 4,4'-BPDA isomers and from 0 to 50 wt % of 3,3' and/or 2,X' (where X' is 2', 3' or 4')-BPDA isomers based on the total weight of BPDA compounds in the crude product.

However, in addition to the desired BPDA, the crude product from the oxidation of DMBP will generally inherently contain certain impurities, such as side products, intermediates, and residual oxidation catalyst. Generally, the impurities comprise one or more isomers of formylbiphenylcarboxylic acid (FBCA), as illustrated by the following formula:

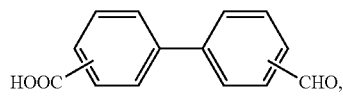

which can be present in levels as high as 50 wt %, more commonly 20 wt % or less, such as 5 wt % or less, or 1 wt % or less, of the crude oxidation product, together with some quinone and fluorenone derivatives. Similarly to the desired BPDA, the relative amounts of the FBCA isomers in the crude product will vary depending on the composition of the oxidized DMBP stream. For example, in the oxidation of a 4,4' DMBP rich stream, 4,4' FBCA will be the predominant FBCA isomer, e.g., greater than 50 wt % based on the total weight of FBCA compounds in the crude product. Typically, the crude product will contain from 50 to 100 wt % of 3,4'- and/or 4,4'-FBCA isomers and from 0 to 50 wt % of 3,3'- and/or 2,X' (where X' is 2', 3' or 4')-FBCA isomers based on the total weight of FBCA compounds in the crude product.

Figure 2:
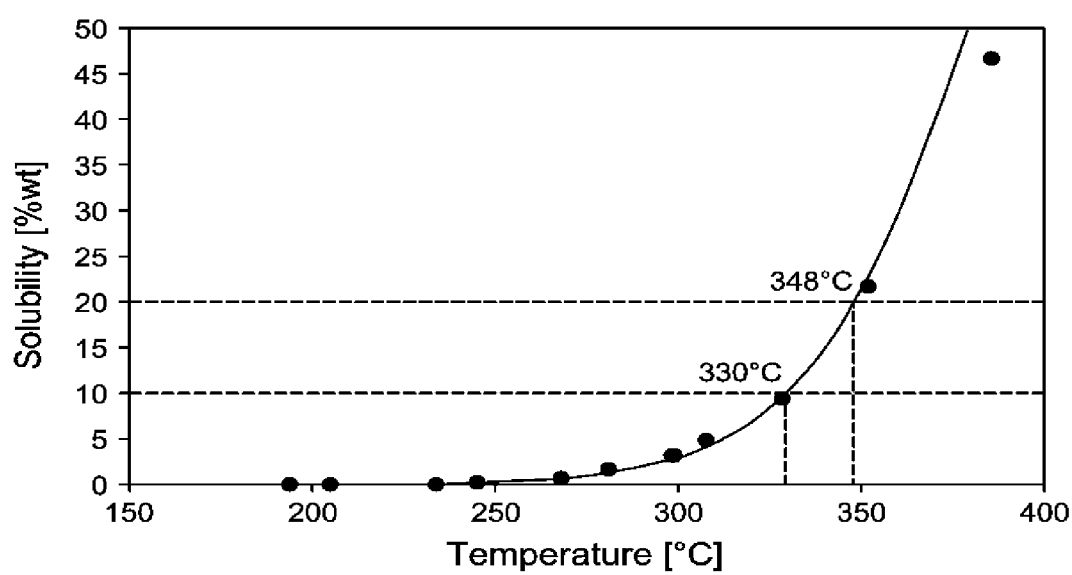
FIG. 2 is a graph of the solubility versus temperature for 4,4'-biphenyldicarboxylic acid in water.

Most of the aforementioned impurities are not desired in the finished product as they will induce low molecular weight (by chain termination) and detrimental color when the BPDA is polymerized. Removal or reduction in concentration of these impurities is therefore required, but common separation methods are generally ineffective. For example, 3,4' and 4,4'-BPDA each have extremely reduced volatility which makes purification via distillation impractical. Additionally, it has been found that, as a result of their common geometry, the impurity 4,4'-FBCA forms a solid solution with 4,4'-BPDA. Similarly, it is further expected that the impurity 3,4'-FBCA forms a solid solution with 3,4'-BPDA. Accordingly, purification via crystallization is not effective either. To obviate or reduce these problems, the present processes include the additional steps of combining the crude BPDA product separated from the oxidation mother liquor, e.g., via filtration, with a suitable liquid, such as water or a water-containing liquid, and then contacting the resultant mixture, typically a solution or slurry, more preferably an aqueous solution or slurry, with a hydrogenation catalyst in presence of hydrogen under conditions effective to selectively reduce at least a portion of the FBCA to hydroxymethylbiphenylcarboxylic acid (HBCA) and/or methylbiphenylcarboxylic acid (MBCA). The reduction conditions should include a temperature high enough so that the BPDA remains in the liquid phase, e.g., dissolved in solution or suspended in slurry, at a loading of at least 5 wt %, such as at least 10 wt %, and preferably at least 20 wt %, to achieve economically viable conversion levels without excessive loss in yield. FIG. 2 plots the water solubility against temperature of 4,4'-BPDA, from which it will be seen that, using water as a solvent, the reduction is preferably conducted at a temperature of at least 270° C. to achieve a suitable BPDA solubility in the liquid phase, more preferably at least 300° C., even more preferably at least 320° C. (corresponding to ca. 10 wt % BPDA loading in the aqueous phase), and ideally at least 340° C. (corresponding to ca. 20 wt % BPDA loading in the aqueous phase). For example, the reduction can be conveniently conducted at a temperature from 270° C. to 360° C., such as from 300 to 350° C., such as from 320 to 340° C. In the case of 3,4'-BPDA, the preferred reduction temperature is from 250 to 300° C.

The catalyst employed for the hydrogenation reaction is preferably chosen so that, at the conditions employed, the catalyst selectively reduces the FBCA without compromising the yield in BPDA. Suitable catalysts include at least one metal or compound thereof from Groups 8 to 11 of the Periodic Table, such as palladium, platinum, rhodium or a compound thereof. The metal content is not critical, but may conveniently range from 0.1 to 10 wt %, such as from 3 to 5 wt %, based on the total weight of the catalyst. In a preferred embodiment, the catalyst comprises palladium on a carbon support. Hydrogen feed rates are not critical, but typically can range from 1 to 10 mols per mol of FBCA in the feed, such as from 1 to 5 mols or from 2 to 3 mols per mol of FBCA.

Using the hydrogenation step described above, the level of the one or more FBCA isomers, preferably 3,4'- and/or 4,4'-FBCA isomers, such as 4,4'-FBCA isomers, in the crude oxidation product can be reduced from up to 5 wt % to less than 200 ppmw, preferably less than 20 ppmw. In addition, color-producing compounds in the crude product, such as quinone derivatives and fluorenone derivatives, can be effectively eliminated via saturation to non-color-producing compounds.

After the reduction step, without wishing to be bound by theory, it is believed that the difference in geometry between BPDA and the resulting HBCA or MBCA due to the sp³ carbon substituent prevents the formation of a solid solution of these impurities in the BPDA crystal, therefore allowing purified BPDA (containing less than 200 ppmw, preferably less than 20 ppmw FBCA, HBCA and/or MBCA) to be recovered from the hydrogenation effluent by conventional separation methods known in the art, preferably crystallization. Generally, such separation, e.g., crystallization, is further effective in removing any remaining amounts of color producing bodies in the hydrogenation effluent, particularly residual amounts of the oxidation catalyst and/or promoter. Preferably, the hydrogenation effluent may be separated via crystallization to form a purified BPDA product and a crystallizer mother liquor comprising the separated HBCA and/or MBCA and optionally, trace amounts of the oxidation catalyst and/or promoter. In such aspects, the crystallizer mother liquor may be recycled to form at least a portion of the liquid phase in the crude BPDA mixture. Optionally, the recycled mother liquor stream may be purged, on a periodic or continual basis, to prevent buildup of color body impurities.

In this way, from a crude biphenyldicarboxylic acid product containing at least 0.05 wt % of formylbiphenylcarboxylic acid, it is possible to separate a purified biphenyldicarboxylic acid diester containing less than 200 ppmw of formylbiphenylcarboxylic acid, hydroxymethylbiphenylcarboxylic acid, and/or methylbiphenylcarboxylic acid, preferably less than 20 ppmw of formylbiphenylcarboxylic acid, hydroxymethylbiphenylcarboxylic acid, and/or methylbiphenylcarboxylic acid.

The purified BPDA diacid can then be fed directly to polymerization or esterified to form purified diester for subsequent polymerization.

Particularly preferably, polyesters may be prepared from the purified BPDA diester or diacid, ether by conventional direct esterification or transesterification methods. Suitable diols for reaction with the above-mentioned diester or diacid compositions include alkanediols having 2 to 12 carbon atoms, such as monoethylene glycol, diethylene glycol, 1,3-propanediol, or 1,4-butane diol, 1,6-hexanediol, and 1,4-cyclohexanedimethanol. Optionally, the BPDA diester or diacid compositions may be further reacted with terephatlic acid or terephthalate. Suitable catalysts include but not limited to titanium alkoxides such as titanium tetraisopropoxide, dialkyl tin oxides, antimony trioxide, manganese (II) acetate and Lewis acids. Suitable conditions include a temperature 170 to 350° C. for a time from 0.5 hours to 10 hours. Generally, the reaction is conducted in the molten state and so the temperature is selected to be above the melting point of the monomer mixture but below the decomposition temperature of the polymer. A higher reaction temperature is therefore needed for higher percentages of biphenyl dicarboxlic acid in the monomer mixture. The polyester may be first prepared in the molten state followed by a solid state polymerization to increase its molecular weight or intrinsic viscosity for applications like bottles.

Process

The present inventive processes will now be more particularly described with reference to FIG. 1, illustrating an embodiment of the present inventive processes, in which the crude BPDA (cBPDA) product is dissolved or suspended in water and hydrogenated. Referring to FIG. 1, a stream of crude BPDA containing one or more isomers of FBCA as an impurity and separated from a mother liquor oxidation product of one or more DMBP compounds, e.g., via filtration (not shown) is fed via line 11 to a mixture tank 12 where the crude BPDA stream is dissolved or suspended in water. The resulting BPDA mixture, e.g., solution or slurry, is supplied by line 13 to a hydrogenation reactor 14 containing a bed of hydrogenation catalyst 15 where the BPDA solution is contacted with hydrogen introduced to the reactor 14 via line 16. Under the conditions maintained in the reactor 14, the one or more isomers of FBCA impurity contained in the crude BPDA are selectively reduced to HBCA and/or MBCA.

The effluent from the hydrogenation reactor 14 is fed by line 17 to a crystallizer 18, where BPDA containing less than 200 ppmw FBCA, HBCA, and/or MBCA is allowed to crystallize out of the effluent. The crystallizer product is then fed by line 25 to a separator 19, where the BPDA crystals are removed via line 21 for further treatment and the crystallizer mother liquor is collected in line 22. Part of the crystallizer mother liquor is then recycled to the mixture tank 12 via line 23, while part is purged from the system via line 24.

The invention will now be more particularly described with reference to the following non-limiting Examples.

HPLC Method

Conversions of the 4,4'-BPDA and 4,4'-FBCA in the following examples were determined using high performance liquid chromatography (HPLC). The samples were analyzed on an Agilent Technologies 1100 Series system equipped with a Phenomenex™ Synergi Hydro-RP phase column (100×2 mm inner diameter and 2.5 µm particles) and DAD detector (254 and 280 nm). The HPLC was performed at room temperature (23° C.) with an eluent rate of 0.4 ml/min. The composition of the mobile phase was 80/20 water (0.1% TFA)/ACN for the initial 10 minutes, and subsequently linearly ramped to 35/65 water (0.1% TFA)/ACN over a period of 40 minutes. The response factor of the different components were determined using 40 ppm dilutions in DMSO.

Examples 1 to 3

The experiments in Examples 1-3 were carried out in a 100 mL stirred autoclave reactor employing palladium on activated charcoal support (5% Pd basis, obtained from Sigma Aldrich (now Millipore Sigma)) as catalyst. Into the reactor, the catalyst, 4,4'-BPDA, 4,4'-FBCA, and water were loaded in the amounts specified in Table 1 at room temperature. The reactor was then purged with nitrogen, tested for leaks by pressuring with nitrogen followed by releasing the pressure, and subsequently pressurized with hydrogen to 20 barg (2000 kPag). Once pressurized to 20 bar, the reactor was heated to 275° C. over a period of 10 minutes, held at the temperature indicated in Table 1 for a period of 60 minutes, and then allowed to cool to room temperature. The reactor was sealed over the course of the heating, holding, and cooling period, thereby allowing the pressure to rise as the temperature increased. After cooling, the reactor contents were filtered to separate liquids from solid fractions using 1 µm particle retaining binder-free glass microfiber filters. Each of the two fractions were analyzed independently of one another by HPLC to assess the BPDA recovery and the FBCA conversion level, with the results summarized in Table 1.

TABLE 1

| Example | Catalyst [mg] | 4,4'-BPDA [mg] | 4,4'-FBCA [mg] | Water [g] | T [° C.] | FBCA conversion [%] | BPDA recovery [%] |
|---|---|---|---|---|---|---|---|
| 1 | 50.0 | 5997.8 | 30.5 | 30.0000 | 350 | 75.9 | 96.1 |
| 2 | 30.0 | 3001.2 | 15.1 | 29.9551 | 330 | 83.4 | 98.7 |
| 3a | 100.0 | 2999.9 | 15.7 | 35.0005 | 330 | >95* | 96.1 |
| 3b | 100.0 | 2.9996 | 15.5 | 34.9959 | 330 | >95* | 92.8 |

*detection limit of HPLC method is 95% conversion

The results in Table 1 demonstrate the effectiveness over a range of catalyst loadings and temperatures of removing FBCA from an aqueous solution of a crude BPDA product and recovering a purified BPDA product.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. All documents described herein are incorporated by reference herein, including any priority documents and/or testing procedures to the extent they are not inconsistent with this text. Likewise, the term "comprising" is considered synonymous with the term "including" for purposes of Australian law and whenever a composition, an element or a group of elements is preceded with the transitional phrase "comprising", it is understood that we also contemplate the same composition or group of elements with transitional phrases "consisting essentially of," "consisting of," "selected from the group of consisting of," or "is" preceding the recitation of the composition, element, or elements and vice versa.

The invention claimed is:

1. A process for purifying a biphenyldicarboxylic acid product containing formylbiphenylcarboxylic acid, the process comprising:
   (a1) contacting a mixture comprising the biphenyldicarboxylic acid product with hydrogen in the presence of a hydrogenation catalyst under conditions effective to selectively reduce at least part of the formylbiphenylcarboxylic acid and produce a hydrogenation effluent comprising (i) hydroxymethylbiphenylcarboxylic acid and/or methylbiphenylcarboxylic acid, and (ii) biphenyldicarboxylic acid, wherein the conditions have a temperature of 320 to 360° C. and the biphenyldicarboxylic acid includes 4,4'-biphenyldicarboxylic acid; and
   (b1) separating at least a portion of the biphenyldicarboxylic acid from the hydrogenation effluent.

2. The process of claim 1, wherein the biphenyldicarboxylic acid includes a mixture of 3,4'-biphenyldicarboxylic acid and 4,4'-biphenyldicarboxylic acid.

3. The process of claim 1, wherein the biphenyldicarboxylic acid product is derived from the catalytic oxidation of at least one dimethylbiphenyl compound.

4. The process of claim 1, wherein the mixture contains at least 5 wt % of the biphenyldicarboxylic acid product.

5. The process of claim 1, wherein the mixture comprises water.

6. The process of claim 1, wherein the mixture is a solution or slurry.

7. The process of claim 1, wherein the hydrogenation catalyst comprises at least one metal or compound thereof from Groups 8 to 11 of the Periodic Table, preferably deposited on a carbon support.

8. The process of claim 7, wherein the hydrogenation catalyst comprises at least one of palladium, platinum, rhodium or a compound thereof.

9. The process of claim 1, wherein the separating (b1) comprises crystallization.

10. The process of claim 1, wherein the biphenyldicarboxylic acid product contains at least 0.05 wt % of formylbiphenylcarboxylic acid and the biphenyldicarboxylic acid separated in (b1) contains less than 200 ppmw of formylbiphenylcarboxylic acid, hydroxymethylbiphenylcarboxylic acid, and/or methylbiphenylcarboxylic acid.

11. The process of claim 10, wherein the biphenyldicarboxylic acid separated in (b1) contains less than 20 ppmw of formylbiphenylcarboxylic acid, hydroxymethylbiphenylcarboxylic acid, and/or methylbiphenylcarboxylic acid.

12. A polyester product comprising the reaction product of a diol with at least one of the following;
   (i) the biphenyldicarboxylic acid separated in (b1) according to claim 1; and/or
   (ii) a biphenyldiester product formed from the esterification of the biphenyldicarboxylic acid separated in (b1) according to claim 1.

13. A process for producing 3,4'-biphenyldicarboxylic acid, the process comprising:
   (a2) contacting 3,4'-dimethylbiphenyl with a source of oxygen in the presence of an oxidation catalyst to produce an oxidation product comprising 3,4'-biphenyldicarboxylic acid and one or more isomers of formylbiphenylcarboxylic acid;
   (b2) combining at least a portion of the oxidation product with a liquid to produce a product mixture;
   (c2) contacting the product mixture with hydrogen in the presence of a hydrogenation catalyst and under conditions effective to selectively reduce at least part of the formylbiphenylcarboxylic acid and produce a hydrogenation effluent comprising (i) hydroxymethylbiphenylcarboxylic acid and/or methylbiphenylcarboxylic acid, and (ii) 3,4'-biphenyldicarboxylic acid wherein the conditions have a temperature of 250 to 300° C.; and
   (d2) separating at least a portion of the 3,4'- and/or 4,4'-biphenyldicarboxylic acid from the hydrogenation effluent.

14. The process of claim 13, wherein the product mixture contains at least 5 wt % of the oxidation product.

15. The process of claim 13, wherein the product mixture comprises water.

16. The process of claim 13, wherein the product mixture is a slurry or a solution.

17. The process of claim 13, wherein the hydrogenation catalyst comprises at least one metal or compound thereof from Groups 8 to 11 of the Periodic Table.

18. The process of claim 17, wherein the hydrogenation catalyst comprises palladium, platinum, rhodium or a compound thereof.

19. The process of claim 13, wherein the separating (d2) comprises crystallization.

20. The process of claim 13, wherein the contacting (a2) is carried out in a solution of the 3,4'-dimethylbiphenyl in a solvent.

21. The process of claim 20, further comprising:
   (e2) separating the oxidation product into a first fraction enriched in the 3,4'-biphenyldicarboxylic acid and the one or more isomers of formylbiphenylcarboxylic acid as compared with the oxidation product and a second fraction enriched in the solvent as compared with the oxidation product; and
   (f2) supplying at least part of the first fraction as the portion of the oxidation product to the dissolving of (b2).

22. The process of claim 1, wherein the conditions have a temperature of 320 to 340° C.

* * * * *